United States Patent [19]

Collins

[11] Patent Number: 4,657,933

[45] Date of Patent: * Apr. 14, 1987

[54] TOPICAL PREPARATION AND METHOD FOR TREATING HERPES SIMPLEX VIRUS INFECTION

[76] Inventor: Harvey T. Collins, 1486 E. 56th St., Chicago, Ill. 60637

[ * ] Notice: The portion of the term of this patent subsequent to Apr. 14, 2004 has been disclaimed.

[21] Appl. No.: 711,130

[22] Filed: Mar. 13, 1985

Related U.S. Application Data

[63] Continuation of Ser. No. 410,492, Aug. 23, 1982, abandoned, and a continuation of Ser. No. 410,493, Aug. 23, 1982, abandoned, and a continuation-in-part of Ser. No. 122,307, Feb. 19, 1980, abandoned, which is a continuation-in-part of Ser. No. 941,043, Sep. 11, 1978, abandoned.

[51] Int. Cl.[4] ............................................. A61K 31/08
[52] U.S. Cl. ................................... 514/722; 514/934; 514/969
[58] Field of Search ........................ 514/722, 934, 969

[56] References Cited

U.S. PATENT DOCUMENTS 3,949,071  4/1976  Alnor .................................. 424/127
4,020,183  4/1977  Asculai et al. ...................... 514/723

OTHER PUBLICATIONS

The Merck Manual; 10th edition (1961) p. 1759–1760.
The Merck Index; 8th edition (1968) p. 276.

Primary Examiner—Leonard Schenkman
Assistant Examiner—Joseph A. Lipovsky
Attorney, Agent, or Firm—Thomas R. Vigil; Ira J. Schultz; Burton Scheiner

[57] ABSTRACT

A topical preparation for treating an epidermal area of a human being infected with Herpes simplex virus comprising a stable emulsion having from approximately 30% by volume to approximately 50% by volume of anhydrous ethyl ether in a pharmaceutically acceptable coconut oil carrier having most of the free fatty acids thereof removed, said emulsion having a boiling point of at least 100° F. The method for treating in vivo an epidermal area of a human being infected with Herpes simplex virus includes the step of applying to the infected area in an amount sufficient to cover the infected area the topical preparation. In another embodiment of the method heat subsequently is applied to the area to which the topical preparation is applied. In one preferred mode of this embodiment of the method the heat is applied approximately three minutes after the topical preparation is applied and the application of heat maintained for a period of between about 3 and 15 minutes.

32 Claims, No Drawings

TOPICAL PREPARATION AND METHOD FOR TREATING HERPES SIMPLEX VIRUS INFECTION

CROSS REFERENCE TO RELATED APPLICATIONS

This application is a continuation of applications Ser. Nos. 410,492 and 410,493, both now abandoned, filed on Aug. 23, 1982, which applications each are a continuation-in-part of application Ser. No. 122,307, now abandoned, filed on Feb. 19, 1980 and entitled Method and Topical Preparation for Treating Herpes Simplex Virus which is a continuation-in-part of application Ser. No. 941,043, now abandoned, filed on Sept. 11, 1978 and entitled Method and Topical Preparation for Treating Herpes Simplex Virus, now abandoned.

TECHNICAL Field

The present invention relates to a method for treating Herpes simplex virus and to a topical preparation for application to areas of the human body infected by Herpes simplex virus for inactivating the virus.

BACKGROUND ART

There are two types of Herpes simplex virus which produce a variety of clinical manifestations. In general, Herpes simplex type 1 is associated with recurrent labialis (cold sores) and Herpes simplex type 2 is associated with recurrent vulvovaginitis.

Herpes simplex virus appears to find the spongy area around mucus membranes an attractive place to thrive and cause infectivity. Once the integrity of an area is violated by Herpes simplex virus, there seems to be a triggering mechanism that welcomes repeated infection of the same area. The reason for this phenomenon occurring is not known at present.

Herpes simplex virus infectivity is primarily dependent upon the intactness of the viral envelope and a chemical combination which damages or removes the envelope will reduce infectivity greatly. It is well known that ether is extremely successful in producing this effect. However, the normal body temperature is about 4° C. above the boiling point of ethyl ether such that treatment in vivo heretofore has not been successful. See for example "Topical Ether and Herpes Simplex Labialis" by Mary E. Guinan, M.D., Ph.D., et al. JAMA, Mar. 14, 1980, Vol. 243, No. 10, pp. 1059-61. Also, due to the extreme instability of ether, particularly ethyl ether, at room temperature or higher, ethyl ether has heretofore only been used for this type of treatment in a controlled environment such as a hospital or physician's office, and ethyl ether has not been available in a form suitable for use outside of a controlled (e.g., hospital) environment.

Rather, ether-, amide-, or ester-linkage compounds, alone or in combination, have been used, However, the effectiveness of such compounds in treating Herpes simplex virus is far less than that of a pure ether. An example of an emulsion including such a compound is disclosed in the Asculai et al. U.S. Pat. No. 4,020,183.

According to the teachings of this patent, nonionic surfactants are delivered in a non-irritating carrier such as a lotion or oil to an infected area with the amount of surfactant employed being between 0.5% and 20% by volume.

It has also been proposed in Alnor U.S. Pat. No. 3,949,071 to use an aqueous solution including a base, fatty acids comprising primarily oleic acid, and a surface-active agent for treating burns, scalds and other skin irritations. The base is an alkali metal carbonate.

Further it has been proposed in Grove U.S. Pat. No. 2,029,166 to use a topical preparation of a soft soap and stearoptens in a salve for use as a liniment.

Still further, it is known from "A simple proof of the thermodynamic stability of materials taken up by solutions containing solubilizers such as soap", Amer. Chem. Soc. 62, 2855-9 (1940) that ether is thermodynamically stable in soap. More specifically, the colloidal solutions formed from a solution of ther and soap containing small additions of silicate or hydroxide are thermodynamically stable because the vapor pressure is significantly less than that of the free hydrocarbon until the solution is approximately saturated.

Moreover, it is known from Soap Manufacture by J. Davidsohn, et al. published by Interscience Publishers, Inc. New York, p. 495, that coconut oil soap was germicidally more active against Escherichia coli and Eberthella typhosa than other soaps made from natural fats and oils. Also, this text teaches at page 503 that coal tar soaps can be made by adding wood tar to coconut oil soap and at page 505 that sulphur soap can be made by adding sulphur to coconut oil soap.

As will be described in greater detail hereinafter, the method and topical preparation of the present invention differ from the previously proposed method and preparations in that according to the method of the present invention a topical preparation comprising an emulsion of anhydrous ethyl ether (rather than a linkage compound) wherein the amount of anhydrous ethyl ether used comprises at least 30% by volume of the emulsion and a coconut oil carrier is applied to the infected area. Also, the emulsion uses a coconut oil carrier having a minimum of free fatty acids. Additionally, the method preferably includes the step of subsequently applying heat to the infected area.

DISCLOSURE OF INVENTION

According to the invention there is provided a topical preparation for treating an epidermal area of a human being infected with Herpes simplex virus comprising a stable emulsion having from approximately 30% by volume to approximately 50% by volume of anhydrous ethyl ether in a pharmaceutically acceptable coconut oil carrier having most of the free fatty acids thereof removed, said emulsion having a boiling point of at least 100° F.

Further according to the invention there is provided a method for treating in vivo an epidermal area of a human being infected with Herpes simplex virus comprising the step of applying to the infected area in an amount sufficient to cover the infected area a topical preparation including a stable emulsion having from approximately 30% by volume to approximately 50% by volume of anhydrous ethyl ether in a pharmaceutically acceptable coconut oil carrier having most of the free fatty acids removed, said emulsion having a boiling point of at least 100° F.

In another embodiment of the method heat subsequently is applied to the area to which the topical preparation is applied. In one preferred mode of this embodiment of the method the heat is applied approximately three minutes after the topical preparation is applied and the application of heat maintained for a period of between about 3 and 15 minutes.

BEST MODE FOR CARRYING OUT THE INVENTION

In accordance with the teachings of the present invention, a topical preparation including an emulsion of anhydrous ethyl ether and a coconut oil carrier having most of the free fatty acids removed has been found to be useful in treating epidermal areas infected with Herpes simplex virus.

According to the method of the present invention a stable emulsion of at least 30% by volume of anhydrous ethyl ether in a pharmaceutically acceptable coconut oil carrier with most of the free fatty acids removed is applied to the infected area. Preferably, heat is also applied to the infected area some time after the application of the topical preparation for a period of 3 to 15 minutes.

It has been known for some time that ethyl ether is very helpful in treating the "cold sore" lesion in an epidermal area infected by Herpes simplex virus. In this respect, the ether damages or removes the viral envelope thereby reducing infectivity. However, ether, particularly ethyl ether, is extremely unstable and has a very low boiling point. Accordingly, one must be very careful in applying ethyl ether and in the past this has only been done in a controlled environment such as in a hospital outpatient ward or in a physician's office. Also, the ethyl ether evaporates quickly and as a result does not penetrate deeply into the infected area.

In veiw of the rapid evaporation of ether, it has been proposed in U.S. Pat. No. 4,020,183 to apply an ether-linkage compound in a non-irritating carrier such as a lotion or oil to the infected area. In this way the ether-linkage compound can be maintained on the infected area for a significant period of time to allow penetration by the ether-linkage compound. However, the ether-linkage compound is not as strong and effective as ethyl ether in destroying the viral envelope.

Thus, according to the teachings of the present invention, anhydrous ethyl ether which is a highly volatile chemical, is utilized. However, it must be combined with a carrier so that it will be more stable. Anhydrous ethyl ether is used because it is believed to afford deeper penetration than other ethers or ether-linkage compounds having a higher boiling point. Also, ethyl ether is more readily available for use in the anhydrous form than are other ethers such as methyl ether, which has a lower boiling point. Anhydrous ethyl ether has virtually no (0.01%) water. Thus, by using anhydrous ethyl ether, the infected area is kept as dry as possible. In this respect, moisture appears to be a deterent to the healing process of the "cold sore" lesion in an area infected with Herpes simplex virus when applying ether thereto.

The anhydrous ethyl ether utilized in the method of the present invention has the following American Chemical Society specifications:

| | |
|---|---|
| Butylated Hydroxy-toluene (preservative) | 0.5–1 ppm |
| Assay $(C_2H_5)_2$ o by CC | 98.5% |
| Color (APHA) | 10 |
| Density (gm/ml at 25° C. Max) | .7079 |
| Peroxide (as $H_2O_2$) | .0001% |
| Residue after evaporation | .001% |
| Substances darkened by $H_2SO_4$ | Passable |
| Alcohol ($C_2H_5OH$) | .01% |
| $H_2O$ (Karl Fisher) | .01% |
| Trace Impurities | PPM |
| Acid (as $CH_3COOH$) | .5 |
| Copper | .1 |

-continued

| | |
|---|---|
| Heavy metals ($A_5PB$) | .1 |
| Nickel ($N_1$) | .1 |

Further according to the teachings of the present invention, coconut oil with most of the free fatty acids removed is used as the carrier. Although other natural oils could be used, coconut oil was found to be the most suitable for emulsification with the anhydrous ethyl ether.

The coconut oil can be refined and bleached or hydrogenated.

The refined and bleached or hydrogenated coconut oil carrier is obtained in the following manner:

First, coconut oil is refined with caustic soda (NaOH), this process also being known as refining of a glyceride. Here the natural oil (a glyceride) is broken down into glycerol and a soap containing most (at least 95%) of the free fatty acids. The glycerol is retained and this process of removing free fatty acids found in the oil (i.e., palmitic, capric, oleic, linoleic and linolenic acids) makes the carrier much less irritating to the skin. The oil now contains no more than 7% free fatty acids and preferably between 2.5 and 3.5% free fatty acids. It is believed that the refined coconut oil carrier aids in healing the epidermal area around the "cold sore" lesion, which area has been leached of moisture by the anhydrous ethyl ether applications, by sealing that epidermal area to air and water which can be deterents to the healing process.

After the refining, the glycerol is further processed, i.e., it can be hydrogenated, to produce stearic acid (cold cream) and the desired product, refined and hydrogenated coconut oil, the carrier used in the emulsion with the anhydrous ethyl ether. It has been found empirically that the most suitable refractive index of hydrogenation for the carrier is 1.4540±0.0002 at 25° C. and an iodine value of 4.5±0.5.

Refining and hydrogenation of oils are well known processed and the manner in which these processes are carried out is described in the text entitled: *Official and Tentative Methods of the American Oil Chemist's Society* (3rd Ed.) 1976, published by the American Oil Chemist's Society, Champaign, Ill., the disclosure of which is incorporated herein by reference. In this text, refining of oil techniques are described in A.O.C.S. Official Method Cc 8d-55 pages 1-3 and hydrogenation of oil techniques are described in A.O.C.S. Recommended Practice Ca 17-76 pages 1-3.

This hydrogenation process is believed to slow down the development of rancidity of the oil, a common problem of oil based compounds and thus allows a longer shelf and use life.

Refined and bleached or hydrogenated coconut oil which has an iodine value of 4.5±0.5, which has no more than 7% free fatty acids (FFA as oleic) and which has a refractive index of 1.4540±0.0002 at 25° C. is commercially available from:

CPC International
International Plaza
P.O. Box 500
Englewood Cliffs, N.J.,
from its subsidiary
Best Foods
CPC International
2841 S. Kilbourne
Chicago, Ill.

and from:

Capital City Products
1200 Route 46
W. New York, N.J.

One preferred partially hardened refined and bleached (or hydrogenated) coconut oil had the following material specifications:

| Color (Lovibond) | Max. 4.0 Red |
|---|---|
| F.F.A. (as oleic) | Max. 7.0% |
| M.I.U. (Moisture Inert:Dist) | Max. 1.0% |
| Saponification value | Min. 254 |
| [1]Polyunsaturated Acids | Max. 0.40% |
| Iodine Value | 4.5 ± 0.5 |
| Odor | Usual characteristic odor |
| Refractive index | 1.4540 ± 0.0002 |

[1]To be determined by using A.O.C.S. Method Cd 7-58

In the refining of the coconut oil, the free fatty acids are taken off, i.e., the free fatty acids are converted to soap which settles and are taken off as "foots" with glycerols of other fatty acids retained, i.e., the glycerols $C_6$ to $C_{18}$. The hydrogenation thus changes the unstable glycerols, e.g., oleic (unstable) to stearic (stable).

Coconut oil is a mixture of fatty acids of even number molecules $C_6$ through $C_{18-1}$. The amounts of $C_6$ and $C_{20}$ are nil.

| The % distribution is as follows: | |
|---|---|
| Fatty Acid | % |
| $C_6$ (Caproic) | Nil |
| $C_8$ (Caprylic) | 6 ± 1 |
| $C_{10}$ (Capric) | 7 ± 1 |
| $C_{12}$ (Lauric) | 48.5 ± 1.5 |
| $C_{14}$ (Myristic) | 19.0 ± 1.0 |
| $C_{16}$ (Palmitic) | 8.75 ± 0.75 |
| $C_{18}$ (Stearic) | 5.25 ± 0.75 |
| $C_{18-1}$ (Oleic) | 3.00 ± 0.50 |

The free fatty acids in the coconut oil will saponify under certain conditions during the refining of the crude coconut oil while the other components will not.

For example, in one refining process, 500 gm of crude coconut oil is put into a water bath with a mechanical stirrer at a temperature between 30°–35° C. at 250 RPM. Next an amount of 20° Baume NaOH is added to effectively saponify the free fatty acids, e.g., $C_{17}H_{33}COOH$ (oleic acid + NaOH = $C_{17}H_{33}COONa + H_2O$). The molecular weight of the oleic acid is 282.4 and the molecular weight of the sodium hydroxide is 40.

After the amount of NaOH is determined by conventional calculations, it is added to the water bath which is then stirred for 5 minutes. Next, decrease speed to 70 RPM and raise the temperature of the water bath quickly to 50°–53° C. Stir for 10–15 minutes more or until the "foots" (bottom soap) appear to be ready to settle out. Let sit in bath until oil is relatively clear before removing the refined oil.

In bleaching the refined coconut oil, a 60 mesh screen, bleaching earth as per American Oil Chemists Society standards, filter paper (Sargent Welch Grade S 32915-J or equivalent) and rolled cotton are used. The screen is lined with thin layers of rolled cotton and 300 gm of refined oil are allowed to filter into a stainless steel cup which is then placed under a mechanical stirrer. Then, 9 grams of bleaching earth are added and stirred at a temperature of 100° to 110° C. The speed of stirring is fast enough to keep the bleach in suspension for five minutes. Next the solution is filtered through a steel funnel having the filter paper therein and the filtrate of refined and bleached coconut oil is collected in a beaker.

The emulsion of anhydrous etheyl ether and the hydrolyzed and hydrogenated coconut oil or the refined and bleached coconut oil is combined in a ratio of from 1:2 to 1:1, anhydrous ethyl ether by volume to coconut oil by volume with a ratio of 2:3 being preferred.

From numerous tests it was found that by combining the coconut oil with the anhydrous ethyl ether in a ratio of 3:2 by volume, forming thereby a supersaturated emulsion, the normal boiling point of the emulsified ethyl ether is raised to approximately 119° F. This numerical ratio combination of the oil and ether was also observed to produce the least amount of damage, i.e., necrosis, of the viable tissue surrounding the herpetic lesion, while still providing a highly effective agent in destroying the viral envelope.

The emulsion is applied as a topical preparation to the infected area or areas in an amount sufficient to cover the infected area or areas once a day for a period of from one week up to ninety days, if necessary. Empirical measurements indicate that the amount applied is approximately one cubic centimeter (1 cc) for approximately each each ¼ square inch (0.4 square centimeter) of infected surface area. More specifically, the preparation is applied daily until the "cold sore" lesions in the infected area are no longer visible.

Preferably, heat is also applied to the infected area, and it has been observed that the heat application appears to speed up and assist the healing process, i.e., the disappearance of the "cold sore" lesions.

Two types of heat have been used with goods results. One is radiant, infra-red or dry heat and the other is wet heat applied with a hot, wet towel.

The radiant, infra-red heat is applied at a temperature as high as the patient can withstand for a period of 15 to 20 minutes on the morning after the preparation is applied. The infra-red source is positioned 16 inches or more from the infected area on the patient's face with a mask provided over the adjacent facial area, particularly over the eyes, to protect them. The radiant heat appears to assist in drying the lesions and was found to be very effective in drying multiple eruptions.

It is also believed that the application of heat increases the blood supply to the area of infection and increases oxygenation of the tissue in that area so as to aid healing further. Also, increased blood flow caused by application of heat is believed to promote a more rapid removal of the debris left behind as the lesion is destroyed.

As an alternative to infra-red heat, wet heat in the form of hot, wet towels can be applied to the infected area at a temperature as high as the patient can withstand, for a period of 15 to 20 minutes each morning and each evening with the topical preparation being applied only once a day in the evening.

For individuals subject to multiple infections at regular intervals, the topical preparation is applied three times daily for the first five days followed by application of the topical preparation three times a day for the next five days with each such application being followed by application of a hot, wet towel (as hot as the individual can stand) for 3 to 20 minutes three times a day.

In one method of treatment, about 2 cc of the topical preparation is applied to the infected area around, for example, the lips. After three minutes, a wet towel, as hot as is bearable by the patient, is applied to the area for about three minutes.

It is believed that without heat the ether penetrates the infected area as deeply as possible in about three minutes. Then it is believed the heat from the wet towel causes the ether that has penetrated to vaporize allowing it to propel or move up the "trigeminal canal", killing the viruses that hide there in a dormant state and become active later causing recurrent infections. Again, it is believed that about three minutes is a sufficient time to keep the vapors moving in the canal at as sufficient pressure and volume to destroy the virus.

Empirical studies show that one method of treatment is to apply the topical preparation at least once (preferably twice) a day for three days. Then, on the third day, even if the "cold sore" appears to be "cured", the preparation and heat as described above are applied three times a day for at least three days. It is believed that after this period the medication has "won the fight" in killing the virus at the site of infection and the body's immune system can take over the "battle" forcing the virus to escape via the trigeminal canal.

Two individuals who had had on the average one "cold sore" per year during the two years prior to treatment with the method of the present invention were treated with a topical preparation which comprised 60% by volume coconut oil with most of the fatty acids removed and 40% by volume anhydrous ethyl ether and which was applied to the infected area once a day for seven days together with application of radian, infra-red heat once a day on the morning after application of the topical preparation. No recurrence of the "cold sore" lesion was observed for a period of seven years after this treatment.

Eight individuals who had had on the average four "cold sore" lesions per year during the ten year period prior to treatment with the method of the present invention were treated with a topical preparation which comprised 60% by volume coconut oil with most of the fatty acids removed and 40% by volume anhydrous ethyl ether and which was applied to the infected area once a day for ninety days together with application of wet heat by means of hot, wet towels twice a day for ninety days. Subsequent to this treatment, no recurrence of the "cold sore" lesions was observed for a period of 2½ years after treatment. The severity of infection with these individuals was such that on the average two of the four appearances of "cold sore" lesions were multiple lesions.

Another four individuals who had had on the average five "cold sore" lesions per year during the ten years preceeding treatment with the method of the presetn invention were treated with a topical preparation which comprised 60% by volume of coconut oil with most of the fatty acids removed and 40% by volume of anhydrous ethyl ether and which was applied to the infected area once a day for ninety days together with application of wet heat by means of hot wet towels twice a day for ninety days. The severity of the infection with these individuals was such that on the average four out of five appearances of the "cold sore" lesions were multiple lesions. No recurrence of the "cold sores" was observed in these individuals for a period of two years after treatment.

Still another ten individuals who had had on the average two "cold sores" lesions per year during the ten years prior to treatment with the method of the present invention were treated with a topical preparation which comprised 60% by volume of coconut oil with most of the fatty acids removed and 40% by volume of anhydrous ethyl ether and which was applied to the infected area once a day for twenty days together with application of wet heat by means of hot, wet towels twice a day for twenty days. Subsequent to this treatment, no recurrence of the "cold sore" lesions was observed for a period of two years after treatment.

It will be appreciated that with the topical preparation of the present invention a safe means of delivering ethyl ether to an epidermal area infected with Herpes simplex virus is made possible. In this respect, the anhydrous ethyl ether is emulsified in the refined and bleached coconut oil carrier as described above so that the heat instability of the anhydrous ethyl ether is counteracted by the high boiling point of the coconut oil carrier. In this way, the boiling point of the overall emulsion is raised from the normal boiling point of ethyl ether at 34.6° C. (approximately 87° F.) up to approximately 54.5° C. (approximately 119° F.). This increase in the bioling point of anhydrous ethyl ether in the emulsion enables the ethyl ether in the emulsion to be stored more easily and more safely thereby to permit its use outside of the controlled environment of a hospital outpatient clinic or a physician's office.

Also it will be appreciated that by utilizing applications of heat to the infected area in addition to the application of the topical preparation healing of the "cold sore" lesions is enhanced and expedited. as stated above, it is believed this is caused by the increase in blood flow to the infected area as a result of the heat applied thereto.

Another important feature of the present invention is that by using at least 30% by volume of anhydrous ethyl ether in a refined and bleached coconut oil carrier, as opposed to an ether-linkage compound, a stronger agent is used in the treatment of Herpes simplex virus thereby to provide a more effective treatment. In this respect, the anhydrous ethyl ether is more effective than the ether-linkage compounds in destroying the viral envelope of Herpes simplex virus thereby to provide a more effective treatment. In this respect, the anhydrous ethyl ether is more effective than the ether-linkage compounds in destroying the viral envelope and the emulsion enables one to apply a sufficient volume of ethyl ether to the infected area. Moreover, by using anhydrous ethyl ether, virtually no water is placed in contact with the infected area when the ether is applied thereby to aid further the healing process.

Another advantage of the topical preparation of the present invention is the use of refined and bleached coconut oil which has much of the skin irritating free fatty acids removed therefrom. Moreover, the refined and bleached coconut oil carrier serves to protect the infected area during treatment thereof from air and water which are often deterents to the healing process.

From the foregoing description it will be apparent that the method and topical preparation for treating Herpes simplex virus of the present invention have a number of advantages some of which are described above and others of which are inherent in the invention. For example, it has been observed that in treating a cold sore virus according to the teachings of the method of the present invention and utilizing the topical preparation of the present invention, local recurrence of cold sores is greatly minimized if not altogether eliminated, and such prevention of recurrence is greatly desired when treating Herpes simplex virus infectivity.

Moreover, from empirical tests it has been found that the topical preparation applied according to the methods of the present invention is effective in treating in vivo Herpes I, Herpes II, "athlete's foot" fungus, "jock itch" fungus and yeast infections and may be effective in treating Chicken Pox, Acne, Eczema, occlusions and infections of pores (pimples and blackheads), skin rashes and canker sores.

I claim:

1. A method for treating, in vivo, an epidermal area of a human being infected with Herpes simplex virus, comprising the steps of: applying to the infected area, in an amount sufficient to cover the infected area, a topical preparation in the form of a stable emulsion having from approximately 30% by volume to approximately 50% by volume of anhydrous ethyl ether in a pharmaceutically acceptable refined coconut oil carrier, said oil carrier being generally free of free fatty acids and essentially free of water, soaps and stabilizers, said emulsion having a boiling point of at least 100° F.

2. The method of claim 1 wherein said topical preparation is applied to the infected area in the evening at the time the patient retires for the night.

3. The method of claim 1 wherein said coconut oil is refined to have no more than 7% free fatty acids.

4. The method of claim 3 wherein said coconut oil is hydrogenated.

5. The method of claim 4 wherein the refractive index of said hydrogenated coconut oil is 1.4540±0.0002 at 25° C.

6. The method of claim 4 wherein the iodine value of said hydrogenated coconut oil is 4.5±0.5.

7. The method of claim 1 wherein said sufficient amount of topical preparation to be applied to the infected area is approximately 1 cubic centimeter of the topical preparation for approximately each 0.4 square centimeter of infected area.

8. The method of claim 1 wherein said coconut oil is refined and bleached coconut oil.

9. The method of claim 1 wherein the numerical ratio of said coconut oil by volume to said anhydrous ethyl ether by volume in said emulsion is 3:2.

10. The method of claim 9 wherein said emulsion has a boiling point of approximately 119° F.

11. The method of claim 9 wherein said emulsion is supersaturated.

12. The method of claim 1, including the step of subsequently applying heat to the area to which the topical preparation is applied.

13. The method of claim 12, wherein said heat applied is wet heat, which wet heat is applied subsequent to rendering the epidermal area generally hydrophobic by virtue of penetration of said topical preparation into the epidermis.

14. The method of claim 13 wherein said heat is applied by means of a wet towel and the temperature of the wet towel is as high as the patient can comfortably withstand.

15. The method of claim 14 wherein said heat is applied about three minutes after said topical preparation is applied for a time period of about three minutes.

16. The method of claim 15 wherein said topical preparation and wet heat are applied three times a day for at least three days.

17. The method of claim 13 wherein said topical preparation is applied three times a day for at least two days without heat and then heat is applied on the third day after an application of said topical preparation followed by applying the topical preparation three times a day for at least three more days and, about three minutes after each application, applying wet heat for about three minutes.

18. The method of claim 13 wherein said topical preparation is applied once a day and said wet heat is applied to the infected area for approximately 15 minutes every morning and evening for a period of at least three weeks.

19. The method of claim 13 wherein said topical preparation is applied once a day and said wet heat is applied twice a day to the infected area until any "cold sore" lesions in the infected area are no longer visible.

20. The method of claim 19 wherein said radiant heat is applied to the infected area at a temperature which the patient can comfortably withstand.

21. The method of claim 12 wherein the heat applied is radiant heat from an infra-red heat source.

22. The method of claim 21 wherein said radiant heat is applied to the infected area for approximately 15 minutes every morning for at least 1 week.

23. The method of claim 21 wherein said topical preparation is applied once a day and said radiant heat is applied once a day to the infected area until any "cold sore" lesions in the infected area are no longer visible.

24. A topical preparation for treating an epidermal area of a human being infected with Herpes simplex virus in the form of a stable emulsion having from approximately 30% by volume to approximately 50% by volume of anhydrous ethyl ether in a pharmaceutically acceptable refined coconut oil carrier, said oil carrier being generally free of free fatty acids and essentially free of water, soaps and stabilizers, said emulsion having a boiling point of at least 100° F.

25. The topical preparation of claim 24 wherein said coconut oil is refined to have no more than 7% free fatty acids.

26. The topical preparation of claim 24 wherein said coconut oil is hydrogenated.

27. The topical preparation of claim 26 wherein the refractive index of said hydrogenated coconut oil is 1.4540±0.0002 at 25° C.

28. The topical preparation of claim 26 wherein the iodine value of said hydrogenated coconut oil is 4.5±0.5.

29. The topical preparation of claim 24 wherein said coconut oil is refined and bleached coconut oil.

30. The topical preparation of claim 24 having a boiling point of approximately 119° F.

31. The topical preparation of claim 24 wherein the numerical ratio of said coconut oil by volume to said anhydrous ethyl ether by volume is 3:2.

32. The topical preparation of claim 24 wherein said emulsion is supersaturated.

* * * * *